United States Patent
Higgins et al.

(10) Patent No.: US 10,436,641 B2
(45) Date of Patent: Oct. 8, 2019

(54) SHUTTER ASSEMBLY FOR CALIBRATION

(71) Applicant: DIRAmed, LLC, Columbus, OH (US)

(72) Inventors: Richard J. Higgins, Westerville, OH (US); Brian Lipp, Columbus, OH (US); Don Warren Caudy, Sunbury, OH (US)

(73) Assignee: DIRAMED, LLC, Columbus, OH (US)

( * ) Notice: Subject to any disclaimer, the term of this patent is extended or adjusted under 35 U.S.C. 154(b) by 0 days.

(21) Appl. No.: 15/156,291

(22) Filed: May 16, 2016

(65) Prior Publication Data

US 2017/0131145 A1 May 11, 2017

Related U.S. Application Data

(63) Continuation of application No. 13/363,265, filed on Jan. 31, 2012, now abandoned.

(60) Provisional application No. 61/441,317, filed on Feb. 10, 2011.

(51) Int. Cl.
  *G01J 3/02* (2006.01)
  *G01J 3/28* (2006.01)
  *G01J 3/44* (2006.01)
  *G01N 21/27* (2006.01)

(52) U.S. Cl.
  CPC .......... *G01J 3/0297* (2013.01); *G01J 3/0232* (2013.01); *G01J 3/28* (2013.01); *G01J 3/44* (2013.01); *G01N 21/274* (2013.01)

(58) Field of Classification Search
  CPC .............................. G01N 21/35; G01N 21/359
  See application file for complete search history.

(56) References Cited

U.S. PATENT DOCUMENTS

| | | | | |
|---|---|---|---|---|
| 4,262,205 A | * | 4/1981 | Abu-Shumays | G01N 21/645 250/458.1 |
| 4,834,295 A | * | 5/1989 | Cristiani | F02M 51/005 239/585.5 |
| 5,085,325 A | * | 2/1992 | Jones | B07C 5/3422 209/580 |
| 5,241,179 A | * | 8/1993 | Carrieri | G01N 21/3504 250/253 |
| 5,335,791 A | * | 8/1994 | Eason | B07C 5/3416 209/588 |

(Continued)

*Primary Examiner* — David P Porta
*Assistant Examiner* — Djura Malevic
(74) *Attorney, Agent, or Firm* — Benesch, Friedlander, Coplan & Aronoff LLP

(57) ABSTRACT

Described are a shutter assembly, a spectrometer, and a method for calibrating a spectrometer. For example, the method may include positioning a shutter including a mirror into a first position in an illumination path of an excitation light beam such that a measurement window is blocked. The mirror may be operable to direct at least one of: (1) the illumination path to a spectral calibration material, (2) a first collection path extending from the spectral calibration material, and (3) a second collection path of a spectral calibration light beam. The method may include directing a returned light from the receiving optics unit to an imaging device; processing the returned light at the imaging device into one or more image signals; analyzing and comparing the image signals with approved image signals; and providing an indication of whether the comparative results of the analysis are within acceptable tolerances.

13 Claims, 9 Drawing Sheets

(56) References Cited

U.S. PATENT DOCUMENTS

| | | | | |
|---|---|---|---|---|
| 5,443,164 A * | 8/1995 | Walsh | B07C 5/3416 | 198/836.1 |
| 5,452,084 A * | 9/1995 | Mitchell | G01N 21/65 | 250/282 |
| 5,577,671 A * | 11/1996 | Seppanen | B07B 9/00 | 241/14 |
| 6,621,574 B1 * | 9/2003 | Forney | G01J 3/02 | 250/252.1 |
| 7,502,105 B2 * | 3/2009 | Lee | G01J 3/44 | 356/301 |
| 8,373,081 B2 * | 2/2013 | Ackley | B07C 5/3422 | 209/580 |
| 8,994,934 B1 * | 3/2015 | Nelson | G01N 33/0057 | 356/73 |
| 9,939,318 B2 * | 4/2018 | Goldring | G01J 3/0291 | |
| 2001/0055116 A1 * | 12/2001 | Maczura | G01J 3/02 | 356/326 |
| 2002/0011567 A1 * | 1/2002 | Ozanich | G01J 3/02 | 250/326 |
| 2002/0039186 A1 * | 4/2002 | Rosenberg | G01J 3/02 | 356/432 |
| 2002/0139925 A1 * | 10/2002 | Mitrovic | G01N 21/68 | 250/226 |
| 2004/0160601 A1 * | 8/2004 | Womble | G01N 21/276 | 356/301 |
| 2004/0176922 A1 * | 9/2004 | Samsoondar | G01N 21/4785 | 702/86 |
| 2004/0263825 A1 * | 12/2004 | Stierle | G01S 7/481 | 356/4.01 |
| 2006/0280360 A1 * | 12/2006 | Holub | G01J 3/02 | 382/162 |
| 2007/0133984 A1 * | 6/2007 | Maier | G01J 3/28 | 398/26 |
| 2008/0137060 A1 * | 6/2008 | Skultety-Betz | G01S 7/4811 | 356/4.01 |
| 2010/0321686 A1 * | 12/2010 | Correns | G01J 3/08 | 356/310 |

* cited by examiner

SHUTTER ASSEMBLY FOR CALIBRATION

CROSS-REFERENCE RELATED APPLICATION

This application is a continuation of U.S. patent application Ser. No. 13/363,265, filed Jan. 31, 2012, which claims priority to U.S. Provisional Patent Application No. 61/441,317, filed Feb. 10, 2011, both of which are entirely incorporated herein by reference.

FIELD OF THE INVENTION

The invention relates to a movable shutter assembly for use with a spectrometer and more particularly to a shutter having calibration material associated with it.

BACKGROUND OF THE INVENTION

There has been a long-felt need for systems that accurately and non-invasively measure one or more analytes in a sample, especially for a variety of healthcare procedures. Spectroscopic systems for optically measuring blood analytes, including Raman spectroscopy for measuring glucose levels in blood or tissue of a patient, using a light source such as a laser or a laser diode, are described in U.S. Pat. No. 7,039,448 by Schlegel et al. and in U.S. Patent Publication No. 2008/0316466 by Higgins et al., both assigned to DIRAmed, LLC. Other non-invasive optical techniques for measuring one or more blood components are disclosed in U.S. Patent Publication Nos. 2006/0276697 by Demuth et al., 2007/0049809 by Bechtel et al. and 2007/0060806 by Hunter et al., for example.

In general, spectroscopy typically involves illuminating a sample, such as a portion of a patient's skin, through a measurement window with a beam of optical radiation, preferably coherent monochromatic light from a laser or a laser diode within a spectrometer, and analyzing a selected spectrum of light returned from the sample to the spectrometer. In certain types of spectroscopy, such as Raman spectroscopy, only the light coming back from slightly penetrating the sample contains the relevant spectrum. Light that reflects or bounces off the sample is largely noise rather than useful signal. It is often challenging to achieve an acceptable signal-to-noise ratio, even with well-calibrated systems.

Precise and repeatable calibration of spectrometers is critical to identifying affect proper analysis of light returned from a sample. Conventional calibration typically is a manual process using known standards such as certain chemicals or light sources that are placed at the exterior side of the measurement window in the same location where samples are normally placed.

User safety is another critical issue when using optical radiation sources, especially when a person's eyes may be exposed to potentially harmful radiation. Important guidelines have been set forth by the Center for Devices and Radiological Health (CDRH) of the Food and Drug Administration (FDA) when diagnostic measurements or other medical procedures are performed on a patient. These CDRH guidelines are in addition to those of the American National Standards Institute (ANSI) and include system lockouts, light-tight enclosures, protective goggles and warning labels. These mitigating techniques can be very bulky and encumbering to users.

Internal shutters have been commonly utilized m cameras, spectrometers and other systems requiring control of light into or out of housings. Laser safety shutters, for example, are available from a number of sources including Electro-Optical Products Corporation of Ridgewood, N.Y.

It is therefore desirable to eliminate the need for users to wear protective goggles while using and calibrating spectrometers, and to simplify calibration procedures.

SUMMARY OF THE INVENTION

An object of the present invention is to provide a shutter assembly which both protects a user and enables convenient checking of calibration while it covers a measurement window.

Another object of the present invention is to automate the process of checking the calibration for spectrometers as frequently as desired.

Yet another object of the invention is to enable tuning of a plurality of light sources within a spectrometer.

This invention results from the realization that a calibration check can be performed as frequently as desired within a spectrometer having illumination and collection optical paths while the spectrometer is in a totally closed, light-tight condition by utilizing a shutter that includes one or more calibration materials and/or an element such as an appropriately-shaped mirror that diverts at least one of the optical paths relative to a calibration standard. The shutter is kept in a normally closed position while excitation light is directed to the calibration material on the shutter or is directed relative to the calibration standard so that resulting reflected or emitted light is directed back to the collection optics of the spectrometer. Parameters to be tuned or otherwise calibrated include wavelength and power level of optical radiation. In some embodiments, the power output of each of a plurality of lasers within a spectrometer is calibrated to automatically tune each laser to emit illuminating excitation radiation at substantially the same power level.

This invention features a shutter assembly for use with a spectrometer having at least one source of optical radiation, such as at least one laser, capable of generating an excitation light beam such as a laser beam having an illumination path. The shutter assembly includes a shutter including at least one of (i) at least one calibration material capable of generating a consistent spectrum within wavelengths utilizable by the spectrometer and (ii) a mirror capable of diverting at least one of the illumination path and a collection path relative to a calibration standard capable of generating a consistent spectrum within wavelengths utilizable by the spectrometer. The shutter assembly further includes a mechanism capable of moving the shutter into at least a first position in the path of the light beam and a second position out of the path of the light beam to enable a sample to be analyzed. When the shutter is moved into the first position, at least one of (a) the light beam strikes the calibration material as desired yet remains blocked from further travel, (b) the light beam is diverted by the mirror to the calibration standard, and (c) the collection path is diverted by the mirror to communicate with the calibration standard while the illumination path is blocked.

In some embodiments, the calibration material is a polymer such as polystyrene. In one embodiment, the shutter itself is formed of at least one calibration material either sufficiently opaque to fully block the laser light or backed with an appropriate blocking material such as aluminium foil. In other embodiments, the calibration material is acetanilide or a derivative thereof such as acetaminophen. In certain embodiments, the mechanism includes a solenoid to move the shutter from the first position to the second position, and further includes a spring for biasing the shutter into the first position. In some embodiments, the shutter assembly further includes a retaining element, such as a magnet or a mechanical detent, to encourage the shutter to remain in the first position even if the spectrometer is bumped or rolls over. In one embodiment, the calibration standard includes a light source such as a mercury-argon light source.

This invention also features a spectrometer capable of performing an internal calibration check and having at least one source of optical radiation capable of generating at least one excitation light beam with at least one desired spectral feature, such as wavelength, single or multiple spectral peaks, or power level, and having an illumination path. The spectrometer further includes a shutter having at least one of (i) at least one calibration material capable of generating a consistent spectrum within wavelengths utilizable by the spectrometer and (ii) a mirror capable of diverting at least one of the illumination path and a collection path relative to a calibration standard capable of generating a consistent spectrum within wavelengths utilizable by the spectrometer. The spectrometer further includes a mechanism capable of moving the shutter into at least a first position in the path of the light beam and a second position out of the path of the light beam to enable a sample to be analyzed. When the shutter is moved into the first position, at least one of (a) the light beam strikes the calibration material as desired yet remains blocked from further travel, (b) the light beam is diverted by the mirror to the calibration standard, and (c) the collection path is diverted by the mirror to communicate with the calibration standard while the illumination path is blocked.

In a number of embodiments, the source of optical radiation, such as at least one laser or laser diode, is capable of generating substantially coherent light, preferably having a wavelength in the range of 700 nanometers to 1100 nanometers, more preferably 775 nanometers to 900 nanometers. In some embodiments, a single light source is capable of generating different spectral features at different times, such as sequential tuning, mode hopping, laser chirping or other methods of modifying the spectral features. In certain embodiments, the spectrometer is capable of performing Raman spectroscopy. In a number of embodiments, the light beam has a focal length set for the measurement site, typically on the exterior side of a measurement window and, in the first position of the shutter, the light beam strikes the calibration material at a position that is different from the focal length of the spectrometer such as a position less than the focal length, near the interior side of the measurement window.

This invention further features a method of calibrating a spectrometer, including selecting a shutter having at least one of (i) at least one calibration material capable of generating a consistent spectrum within wavelengths utilizable by the spectrometer and (ii) a mirror capable of diverting at least one of the illumination path and a collection path relative to a calibration standard capable of generating a consistent spectrum within wavelengths utilizable by the spectrometer. The method further includes positioning the shutter in at least a first calibration position in the path of at least one light beam such that at least one of (a) the light beam strikes the calibration material as desired yet remains blocked from further travel to a sample measurement site, (b) the light beam is diverted by the mirror to the calibration standard, and (c) the collection path is diverted by the mirror to communicate with the calibration standard while the illumination path is blocked further travel to a sample measurement site. The method further includes analyzing a selected spectrum of light returned from the calibration material or the calibration standard, comparing results of the analysis with approved results, and providing an indication of whether the results of the analysis are within acceptable tolerances, such as within a desired range of wavelengths or power levels.

In some embodiments, the shutter carries at least two calibration materials, each at a different locus on the shutter, and the shutter is successively positioned in different calibration positions, each calibration position corresponding to one of the loci. In certain embodiments, the light beam has a focal length set for the measurement site and, in the first position of the shutter, the light beam strikes the calibration material at a position that is different from the focal length. The method further includes placing a sample in the measurement site and, if the results of the analysis are within acceptable tolerances, moving the shutter into a second position out of the path of the light beam to take a reading of the sample.

BRIEF DESCRIPTION OF THE DRAWINGS

In what follows, preferred embodiments of the invention are explained in more detail with reference to the drawings, in which.

DETAILED DESCRIPTION F THE PRE REFERRED EMBODIMENTS

Figure 1:
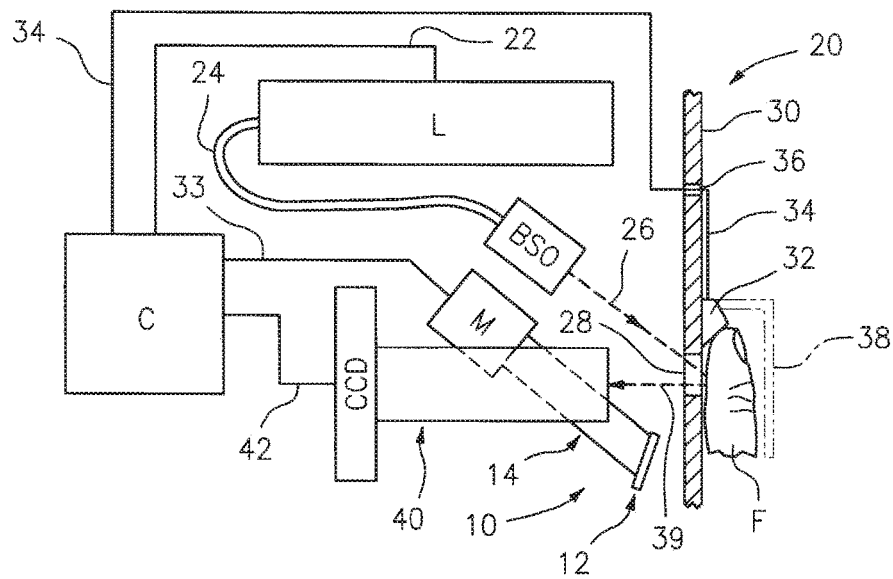
FIG. 1 is a schematic, stylized diagram of a spectrometer utilizing a shutter assembly according to the present invention.

This invention may be accomplished by a shutter assembly for use with a spectrometer having at least one source of optical radiation, such as at least one laser, capable of generating an excitation light beam such as a laser beam with at least one desired spectral feature and having an illumination path. The shutter assembly includes a shutter having at least one of at least one calibration material capable of generating a consistent spectrum within wavelengths utilizable by the spectrometer and (ii) a mirror capable of diverting at least one of the illumination path and a collection path relative to a calibration standard, such as a calibration material or a calibration light source, capable of generating a consistent spectrum within wavelengths utilizable by the spectrometer. The calibration material is carried by the shutter in some constructions and, in other constructions, forms the shutter itself. The shutter assembly further includes a mechanism capable of moving the shutter into at least a first position in the path of the light beam and a second position out of the path of the light beam to enable a sample to be analyzed. When the shutter is moved into the first position, at least one of (a) the light beam strikes the calibration material as desired yet remains blocked from further travel, (b) the light beam is diverted by the mirror to the calibration standard, and (c) the collection path is diverted by the mirror to communicate with the calibration standard while the illumination path is blocked.

The term "optical radiation" is used interchangeably with "light" herein and refers to electromagnetic radiation at wavelengths including ultraviolet (UV), visible, near infrared (NIR) and infrared (IR) spectra. The term "spectrometer" is intended to include spectrophotometers and spectroscopes, as well as systems utilizing spectroscopic or spectrographic techniques to detect and process optical radiation. The term "spectral feature" includes wavelength, frequency and power level.

Shutter assembly 10, FIG. 1, includes a shutter 12 and a mechanism M which includes a support arm 14 and an actuator such as a solenoid or a linear actuator to move support arm 14 with shutter 12 from a first, normally closed position to a second, open position as described in more detail below. Shutter assembly 10 is part of spectrometer 20 having a light source L which in this construction is a Class 3B laser capable of generating coherent monochromatic light, preferably having a wavelength in the range of 700 nanometers to 1100 nanometers, more preferably 775 nanometers to 900 nanometers when Raman spectroscopy is performed. When enabled by controller C through line 22, laser L generates a light beam which is directed through fiber optic cable 24 to beam shaping optics BSO. A shaped light beam 26 is directed through measurement window 28 in housing 30 to strike a sample, such as finger F, placed at a sample measurement site proximate to the exterior surface of window 28.

Finger F of a patient, also referred to herein as a user, is shown in FIG. 1 with the pad of the finger F directly against the exterior surface of window 28. Finger F is pressing against sensor 32 which communicates with controller C through line 34, which passes through housing 30 at a light-tight port 36 in this construction. Activation of sensor 32 confirms that finger F is fully inserted within a finger guide housing 38, shown in phantom. When in the first position, shutter 12 covers the measurement window 28 to block all optical radiation from exiting housing 30. Control of shutter assembly 10, preferably when combined with finger sensor 32 and guide housing 38, provides a lockout mechanism that prevents optical radiation from inadvertently escaping through the measurement window without a finger or other object present to block the optical radiation while spectrometer 20 is actively taking measurements.

With sensor 32 activated, controller C energizes mechanism M through line 33 to move shutter 12 away from measurement window 28 to the second position as shown, and energizes laser L. In another construction, insertion of finger F operates a linkage that moves shutter 12 to the second, open position.

Figure 6:
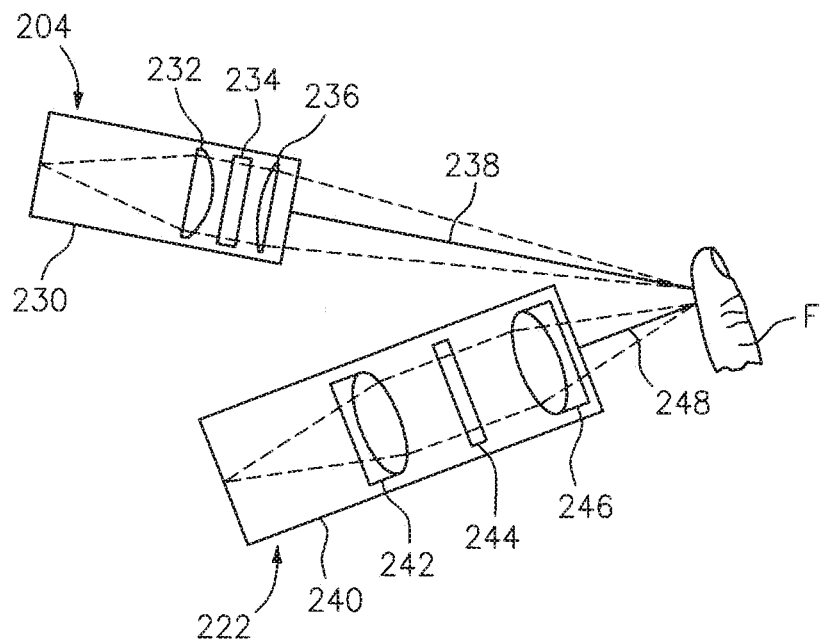
FIG. 6 is a schematic diagram showing the focal lengths for beam shaping optics and receiving optics relative to a finger positioned at a measurement site.

Some of the light returning from the pad of finger F is received as returned optical radiation 39 by receiving optics 40 and directed to a charge-coupled device array CCD or other imaging device such as a camera. Image signals are then provided through line 42 to controller C. One construction of the transmitting and receiving optics is described in more detail in relation to FIG. 6 below. Shutter control logic and system calibration are discussed in relation to FIGS. 9A and 9B below.

Figure 2:
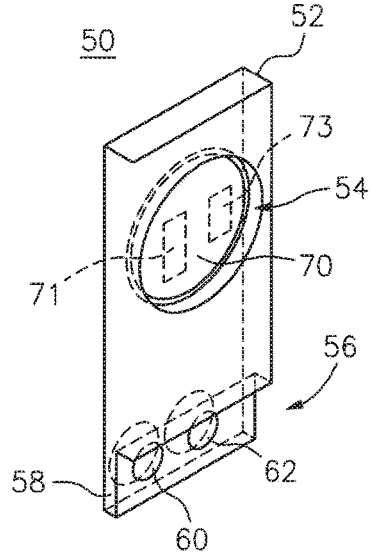
FIG. 2 is an enlarged perspective view of a shutter, detached from the shutter arm, carrying a calibration material according to the present invention.

A shutter 50 according to the present invention is shown in more detail in FIG. 2 machined from an aluminium block 52 to have a width of approximately 0.63 inches, and overall height of approximately 1.44 inches and an overall thickness of 0.13 inches. A circular recess 54 has a diameter of approximately 0.56 inches. A shutter arm mating recess 56 reduces the remaining block thickness of wall 58 to approximately 0.062 inches. Wall 58 defines screw holes 60 and 62 which match with holes 84 and 86, respectively, of shutter arm 80, FIGS. 3A and 3B, described in more detail below.

Calibration material 70, FIG. 2, is carried within recess 54. In another construction, shutter 50 itself is formed of a stable solid calibration material having the appropriate spectral response, either sufficiently opaque to fully block the laser light, which may be accomplished by the addition of a dye or colorant such as carbon black, or backed with an appropriate blocking material such as aluminium foil. In some constructions, the shutter 50 carries at least a second, different calibration material, represented as dashed rectangle 71, and may carry a third calibration material represented as dashed rectangle 73 at a different locus. In yet other constructions, shutter 50 carries an optical diverter element such as a mirror that is described in more detail relative to FIGS. 7 and 8 below. The actual dimensions of shutter 50 including those of recess 54 and calibration material 70, 71 and 73 depend on the size of the measurement window of the spectrometer in which shutter 50 and arm 80 are to be installed as well as the dimensions of the pattern cast by the light beam on shutter 50. In one construction, at least one of the calibration material is a polymer such as a sheet of polystyrene having a thickness of 0.0625 inch and a diameter of 0.56 inch. The material itself may be partially translucent or transparent when mounted in front of an opaque material and, in some constructions, has an unpolished surface finish to promote diffuse scattering. One acceptable polystyrene is a high impact polystyrene such as part number 8734K23 available from McMaster Carr, Chicago, Ill. While a polymer or other stable solid material with appropriate spectral response is preferred because an optically clear container or barrier is not needed to house stable solid material, other suitable calibration materials for Raman spectroscopy include acetanilide or a derivative thereof such as acetaminophen in dry powder or liquid form, preferably in an air tight quartz cuvette or similar container. More than one calibration material can be placed on the shutter at different designated positions as shown by in phantom for elements 71 and 73 or, alternatively, multiple calibration materials can be overlaid or combined in such a way that the respective spectra are captured simultaneously.

Figure 3B:
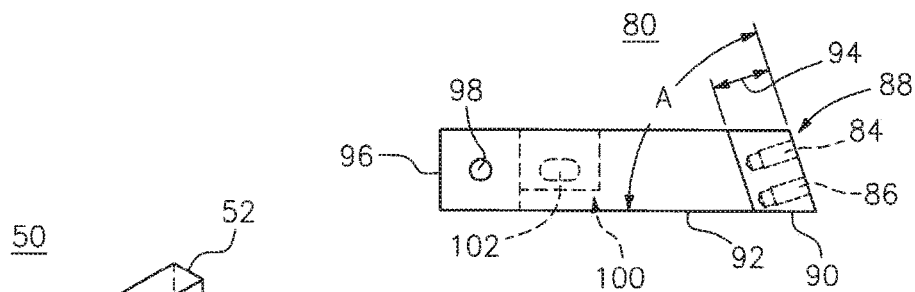
FIG. 3B is a top plan view of the shutter arm of FIG. 3A.
Figure 3A:
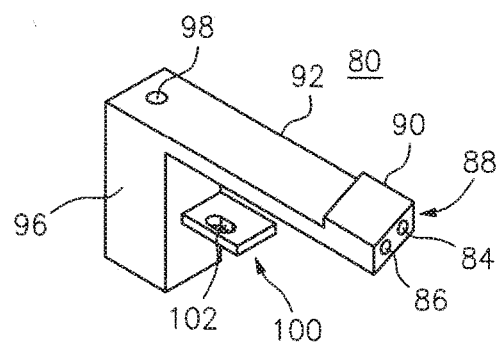
FIG. 3A is an enlarged perspective view of a shutter arm which mates with the shutter of FIG. 2.

Returning to shutter arm 80, FIGS. 3A and 3B, holes 84 and 86 are formed in face 88 of head 90. As illustrated in FIG. 3B, face 88 is preferably oriented at an angle A relative to shaft 92. In one construction, angle A is approximately 70 degrees to 75 degrees. Head 90 has a thickness of approximately 0.19 inches and a depth of 0.37 inches as indicated by arrow 94. Shaft 92 is connected to post 96 which defines a pivot passage 98 about which shutter arm 80 rotates. Post 96 carries a projection 100 which defines opening 102.

Figure 4:
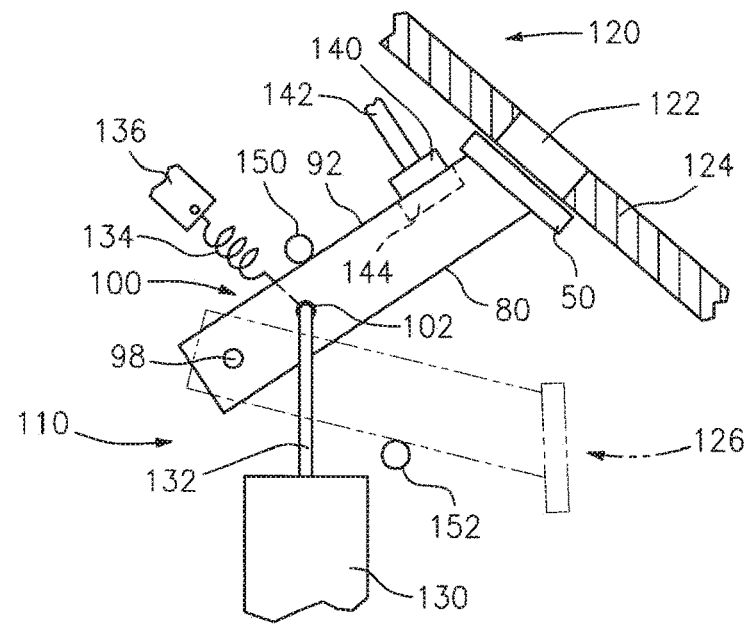
FIG. 4 is a schematic top, partial cross-sectional view of another shutter assembly according to the present invention installed in a spectrometer with a retaining element and a biasing spring which are overcome by a solenoid to move the shutter from a first position to a second position.

Shutter 50 and shutter arm 80 are shown mated as part of shutter assembly 110, FIG. 4, at least a first, closed position within a spectrometer 120 having measurement window 122 through housing 124. Shutter 50 is movable to a second, open position 126, shown in phantom, by a solenoid 130 having arm 132 pivotally connected with opening 102 of projection 100. Solenoid 130 generates sufficient pull to overcome biasing spring 134, attached at one end to mount 136 and at its other end to projection 100, which biases shutter arm 80 with shutter 50 to the normally closed, first position.

When two or more calibration materials are carried by the shutter 50, each at a different locus on the shutter, solenoid 130 is instructed to successively position the shutter in different calibration positions, each calibration position corresponding to one of the loci.

In this construction, shutter arm 80 is further restrained in the first position by a retaining magnet 140, such as a neodymium magnet, mounted on a post 142. When shutter arm 80 is formed of a non-ferromagnetic material such as aluminium, a corresponding ferromagnetic or magnetic element 144, shown in phantom on shaft 92, can be installed. Alternatively, another mechanical retaining element such as a detent is carried on one of post 142 and shaft 92, with the other of post 142 and shaft 92 having a matching recess or other engagement feature.

User safety is augmented by position sensors such as limit switches 150 and 152, which are contacted in this construction by shaft 92 when in the first and second positions, respectively. In other constructions, position sensors are located to contact appropriate edges of shutter 50 or other features on shutter arm 80.

Figure 5A:
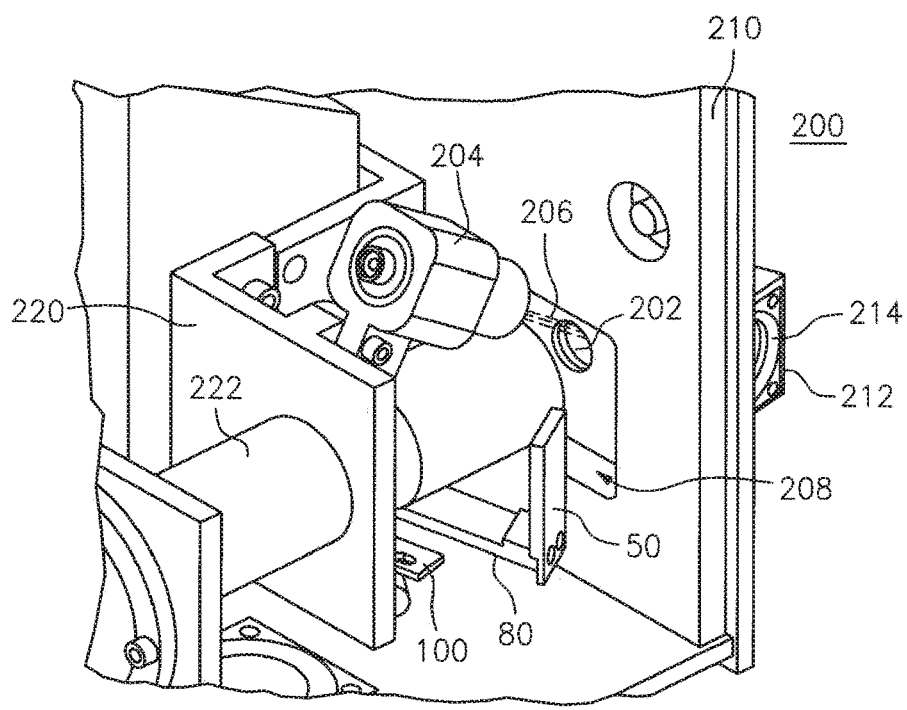
FIG. 5A is a perspective view of a portion of a spectrometer utilizing the shutter components of FIGS. 2-3B according to the present invention in an open configuration.
Figure 5B:
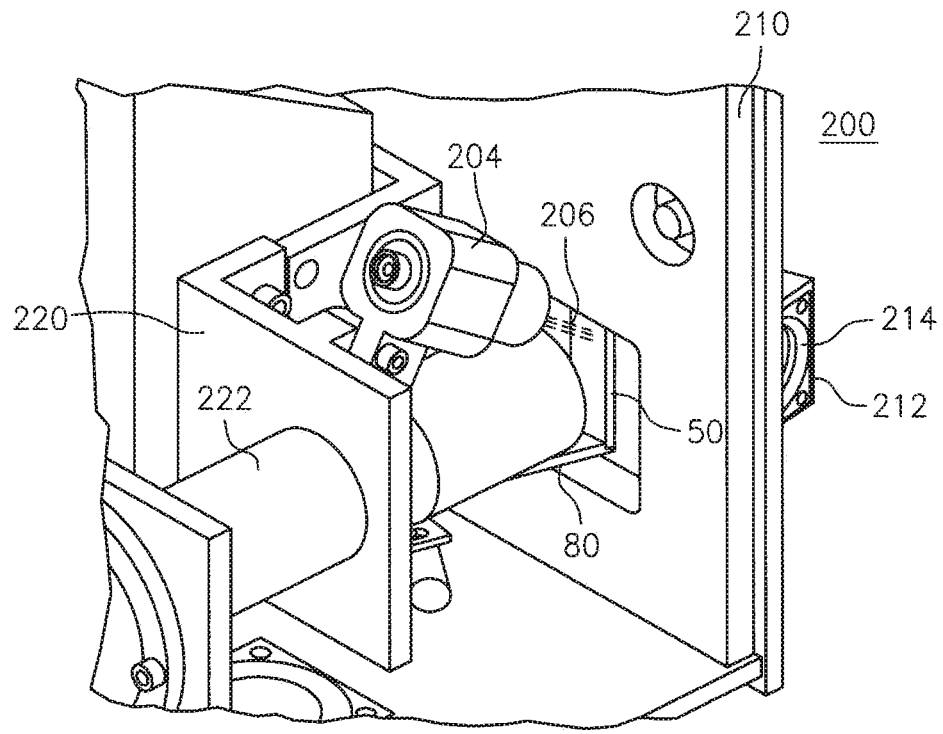
FIG. 5B is a perspective view of the spectrometer of FIG. 5A in a closed configuration enabling automatic calibration according to the present invention.

A more detailed illustration of a spectrometer 200 utilizing shutter 50 according to the present invention is provided in FIGS. 5A and 5B for the first and second positions, respectively, relative to measurement window 202 in recess 208 in housing 210. Beam shaping optics 204 directs shaped light beam 206 through window 202 into finger guide housing 212 which defines an opening 214 for a finger of a user of spectrometer 200. No user is shown in FIG. 5A or 5B for ease of illustration.

Beam shaping optics 204 is shown mounted on a surface of mounting bracket 220 which also supports receiving optics 222. A schematic, simplified diagram of the lenses and resulting focal lengths of these optics is provided in FIG. 6. Housing 230 of beam shaping optics 204 holds lenses 232, 234 and 236 which shape the light beam so that, at a focal length 238, the light beam casts an illumination pattern on finger F approximately in the shape of a narrow rectangle having a height of about 3 mm. In one construction, the length of the rectangular pattern has one or both edges curved, such as to form a somewhat convex pattern. Receiving optics 222 includes a housing 240 which holds lenses 242, 244 and 246 which focus at focal length 248 on the surface of finger F, preferably slightly spaced from the pattern cast by the light beam, to collect optical radiation. Preferred illumination and collection techniques are disclosed in U.S. Patent Publication No. 2008/0316466 by Higgins et al., which is incorporated herein by reference.

Figure 7:
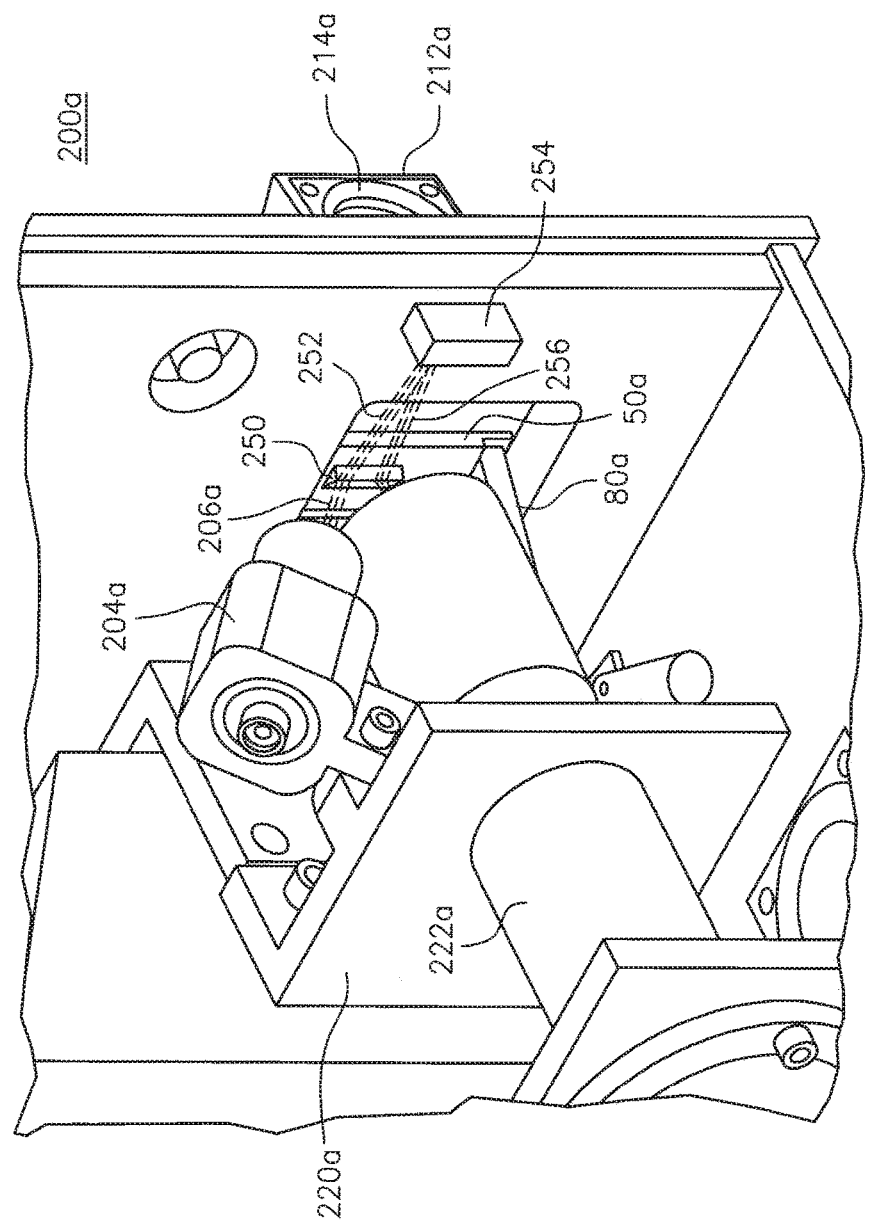
FIG. 7 is a perspective view of an alternative spectrometer having a shutter with a diverting element such as a mirror which redirects the illumination and collection optical pathways to a remote calibration material.

An alternative spectrometer 200a, FIG. 7, includes a shutter 50a on a shutter arm 80a and carrying an angled mirror 250 which reflects light beam 206a from beam shaping optics 204a as a reflected beam 252 to strike a calibration source 254 which, in this construction, is a block of polystyrene. A light beam 256 is collected by receiving optics 222a.

Figure 8:
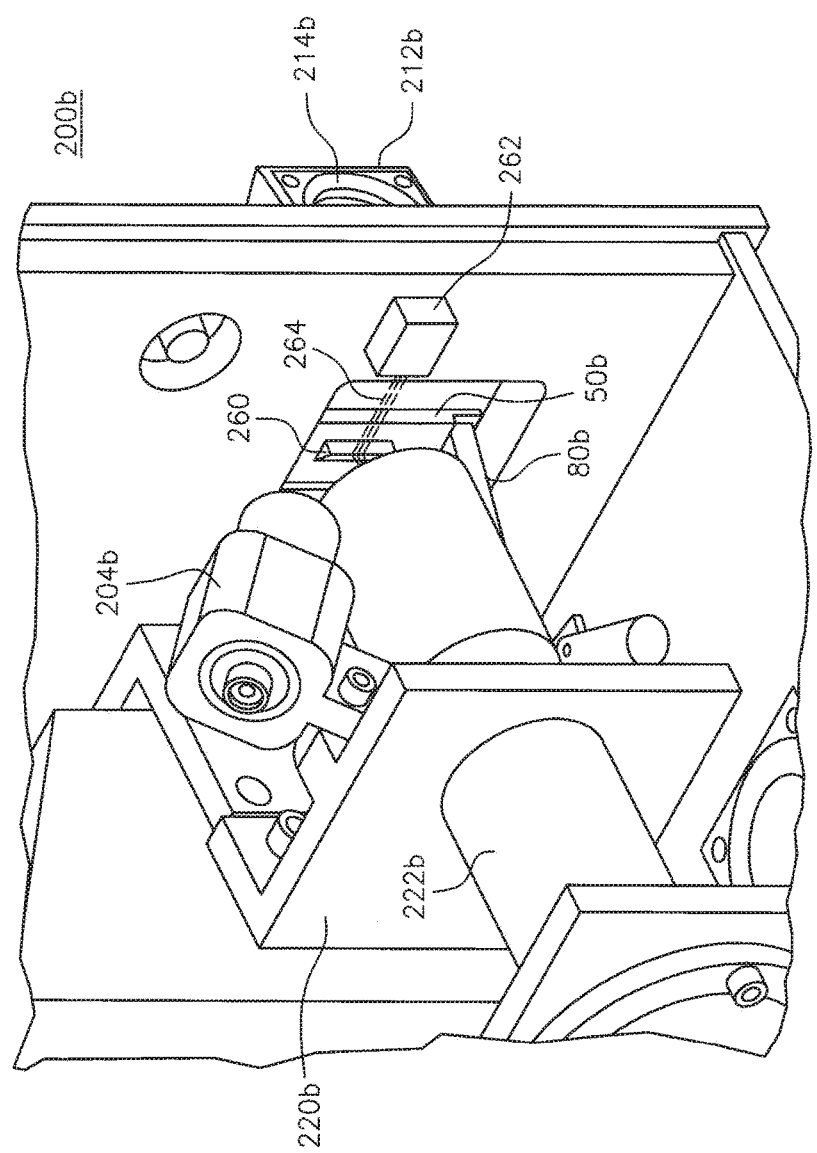
FIG. 8 is a perspective view of yet another spectrometer according to the present invention having a calibration light source such as a helium-argon light.

Yet another alternative spectrometer 200b, FIG. 8, includes a shutter 50b on a shutter arm 80b which blocks light from beam shaping optics 204b in the closed position as shown. A calibration light source 262 such as a helium-argon light source emits a calibration beam 264 which is reflected by angled mirror 260 on shutter 50b into receiving optics 80b. It is preferred to use a calibration light source during servicing of a spectrometer when the calibration light source produces a spectrum that can be utilized to check absolute wavelength registration on a CCD array or other imaging element, along with relative intensity of spectral peaks, which is especially useful for checking optical alignment of a spectrometer. A suitable calibration material such as polystyrene yields a nominally different spectrum that is relative to the main laser source wavelength, power and alignment, and is useful as a general system check subject to more variables.

Figure 9A:
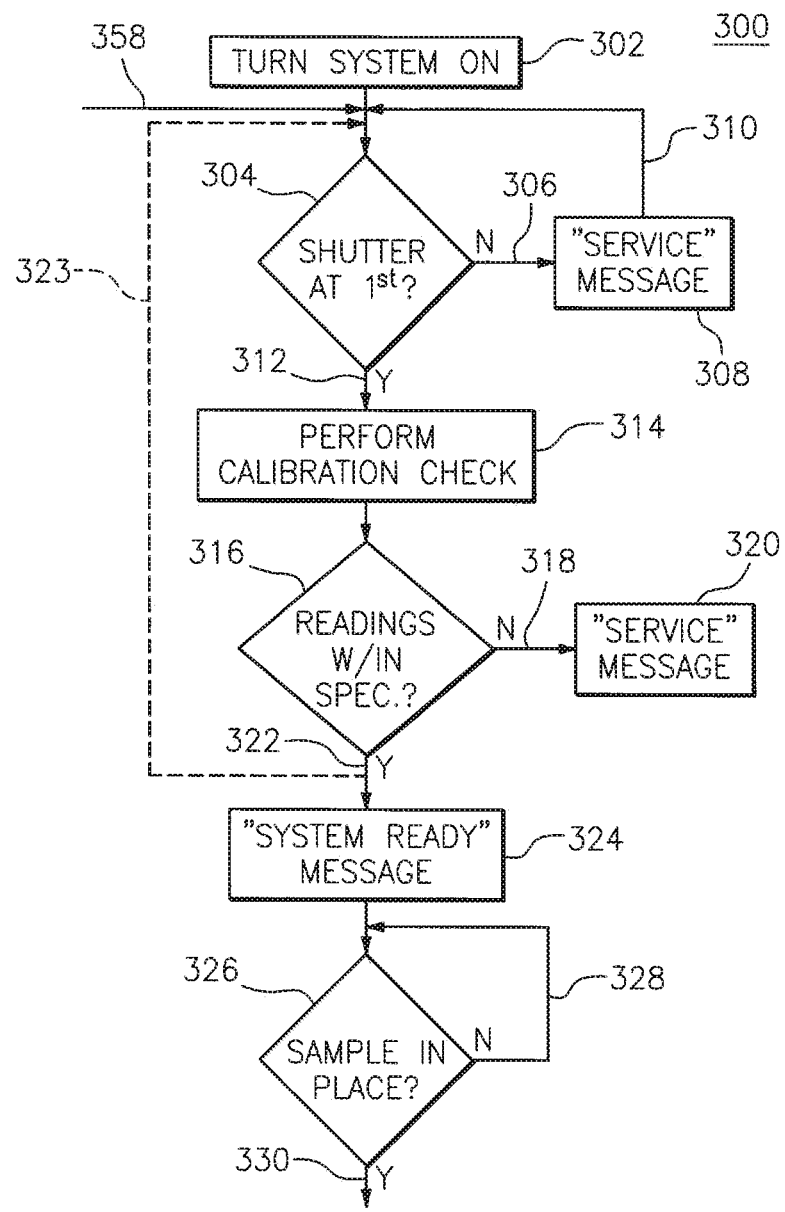
FIGS. 9A-9B are flow charts illustrating shutter control logic for the spectrometer of FIG. 1.
Figure 9B:
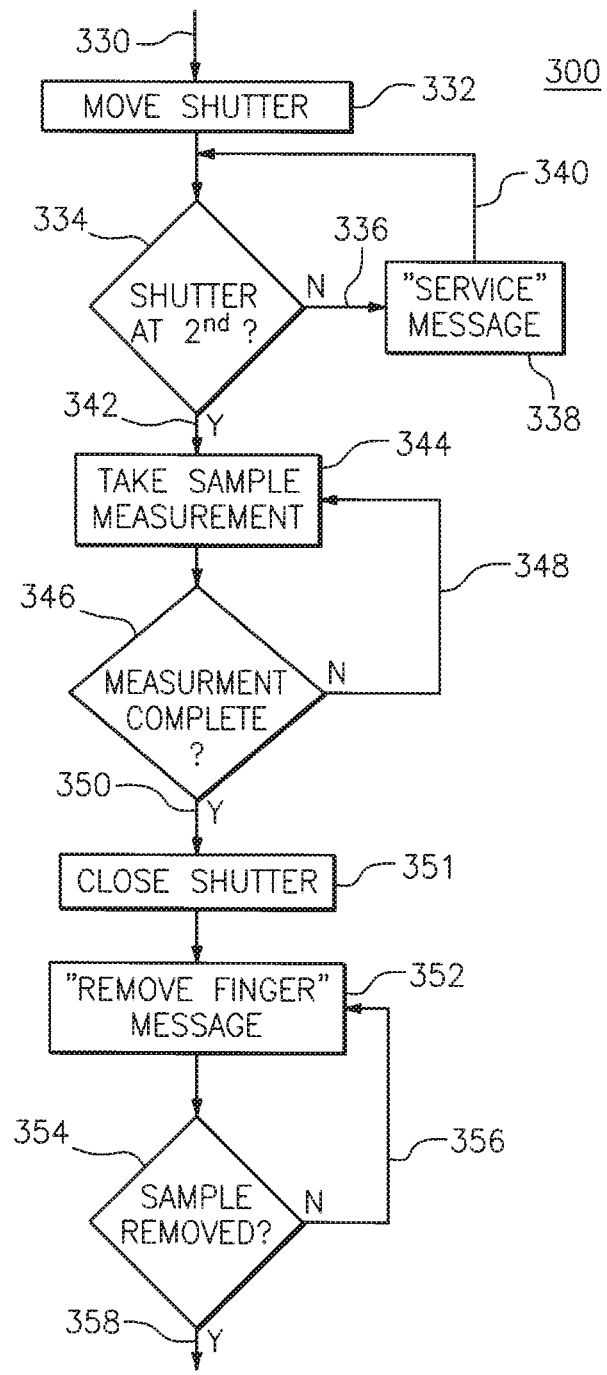

One procedure for operating a spectrometer system according to the present invention is illustrated by shutter control logic 300, FIGS. 9A and 9B. After turning on the system, step 302, and allowing for the system to warm up, the system inquires whether the shutter is positioned at the first calibration position, step 304. If it is not, such as detected by limit switch 150, FIG. 4, then the logic proceeds as shown by arrow 306 to a warning step 308 in which a "service" or "service required"-type message is displayed or otherwise indicated to a user or to an operator. The logic returns, arrow 310, to step 304 until the shutter is confirmed to be at the first calibration position. When the first position is reached, the logic proceeds, arrow 312, to performing an initial calibration check, step 314.

When the shutter carries at least two calibration materials, each at a different locus on the shutter such as shown for materials 70, 71 and 73, FIG. 2, initial calibration check and/or subsequent calibration check may include successively positioning the shutter in different calibration positions, each calibration position corresponding to one of the loci. Position verification steps similar to step 304 can be included in calibration step 314, with warning steps similar to step 308 if the shutter is not mechanically positioned correctly.

After a calibration check using one or more calibration materials has been performed or, in another construction, after each calibration material or calibration standard has been analyzed, the measurement readings are compared, step 316, with stored data for the calibration material or the calibration standard, as appropriate. If the readings are not within specifications, the logic proceeds as shown by arrow 318 to step 320 in which a "service" message or other error indication is provided. Step 320 also represents at least one action to tune or adjust at least one desired spectral feature of at least one light source, such as successively tuning a plurality of lasers to adjust each laser to the same power level, such as the same peak area, as described in more detail below in relation to FIG. 11.

If the measurements are within specifications, the logic proceeds, arrow 322, to display a "system ready" message, step 324. Alternatively, when a plurality of excitation beams are to be calibrated, the logic returns to step 304 as indicated by dashed line 323, and step 314 then includes energizing the next excitation beam. After each excitation beam has been tuned or otherwise calibrated, the logic cycles at step 326 and arrow 328 until a sample such as a finger F, FIG. 1, activates a position sensor 32.

Once a sample is positioned properly, the logic proceeds, arrow 330, to instruct an actuator such as solenoid 130, FIG. 4, to move the shutter, step 332, FIG. 9B. Whether the shutter has reached the second, open position is monitored, step 334, such as by waiting for a signal from sensor 152, FIG. 4. If the position signal is not timely received, the logic proceeds, arrow 336, to step 338 in which a "service" message is provided. Arrow 340 indicates that the system can cycle repeatedly through step 334 until the shutter is confirmed to be in the open position, arrow 342. Measurements of the finger or other sample are then taken, step 344, step 346 and arrow 348, utilizing one or more excitation beams, until the measurements have been completed, arrow 350, and the shutter is closed, step 351. A "remove finger" or similar message is displayed, step 352, and the system continues the display, step 354 and arrow 356, until the finger is removed, arrow 358. Preferably, a post-sampling calibration check is again performed as shown by having the logic return via arrow 358 to step 304, FIG. 9A, as described above.

Figure 10:
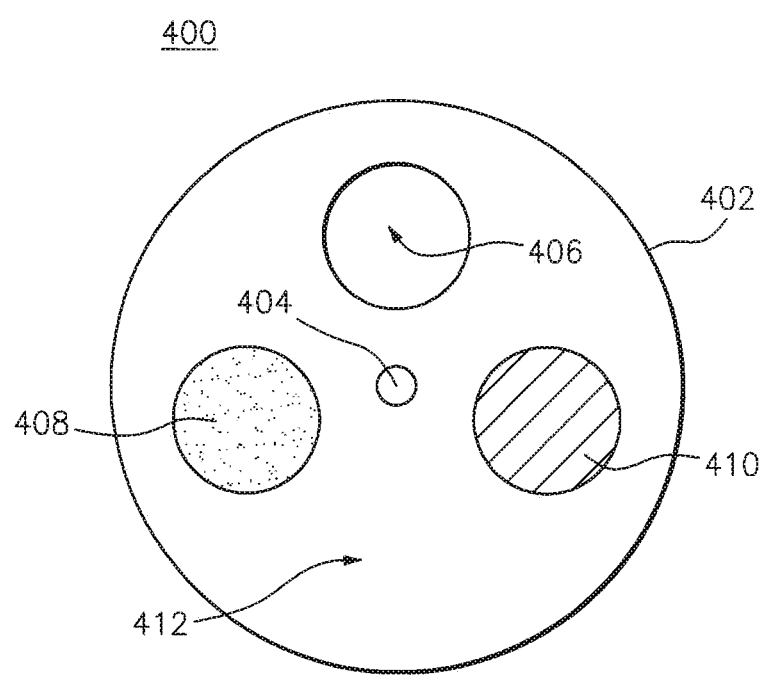
FIG. 10 is a schematic front view of an alternative, rotatable shutter.

While a pivoting type shutter has been described above, this is not a limitation of the invention. Rotatable shutter 400, FIG. 10, includes an aluminium wheel or disk 402 which is driven about a center 404 to different positions according to the present invention. Disk 402 defines an opening 406 which allows a light beam to pass through a measurement window beyond shutter 400. Disk 402 carries first and second calibration material 408 and 410 to enable calibration checks as described above. The remainder of disk 402, such as region 412, serves as a "closed" position to block optical radiation from reaching a measurement window.

Use of a single type of light source is also not a limitation of the invention. The frequency, that is, the number of oscillations per second, of the illumination beam can be shifted, also referred to as Shifted Excitation Raman Differential Spectroscopy, such as described in U.S. Pat. No. 6,281,971 by Allen et al. A tunable filter can be utilized as disclosed in U.S. Pat. No. 7,145,651 by Li et al. Two or more light sources can be incorporated into a spectrometer according to the present invention such as discussed in U.S. Pat. No. 7,558,619 by Ferguson et al. The teachings of these patents are incorporated herein by reference in their entireties.

Figure 11:
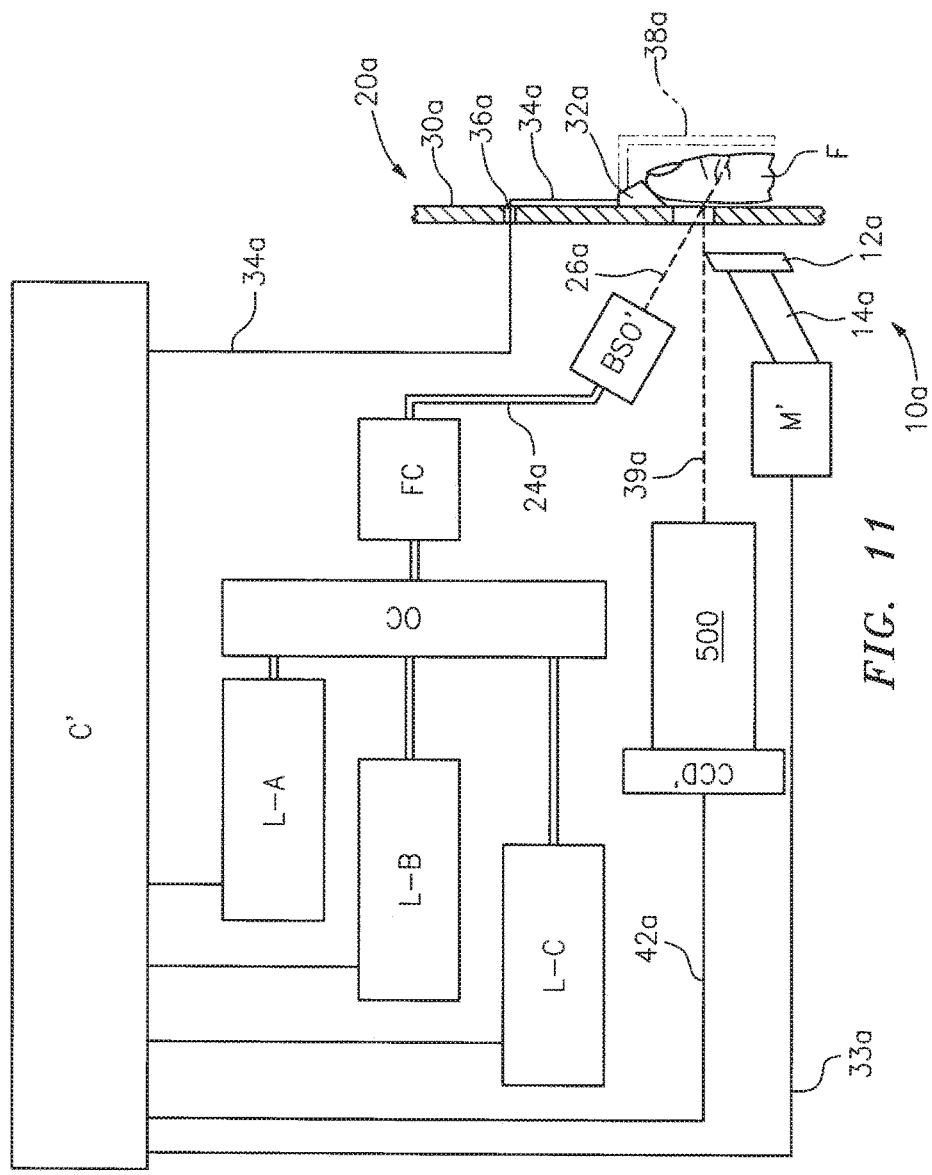
FIG. 11 is a schematic diagram of an alternative spectrometer according to the present invention having multiple light sources.

Shutter assembly 10a, FIG. 11, is installed within spectrometer 20a according to the present invention having three lasers L-A, L-B and L-C and controller C'. Features similar to shutter assembly 10 and spectrometer 20, FIG. 1, are labeled with similar reference numerals. For example, mechanism M', FIG. 11, includes an actuator to move support arm 14a with shutter 12a from a first, normally closed position to an open position as described above for shutter assembly 10, FIG. 1. Differences between spectrometers 20 and 20a include optical combiner OC and fiber conditioner FC which provide a more even distribution of light to beam shaping optics BSO'sequentially from the lasers L-A, L-B and L-C, in whatever firing order is commanded by controller C'. A suitable optical combiner is a 3-UP Octopus optical switch with FC/PC connectorization on one end and SMA on the combiner end, Part No. 1100UMX3-400UMSMA available from Innovative Photonic Solutions of Monmouth Junction, N.J.

Shaped illumination beam 26a strikes finger F and returned optical radiation 39a enters spectroscope 500, such as a Stroker f/1.3 Raman spectrometer series available from Wasatch Photonics, Durham, S.C., and is directed to charge-coupled device array CCD'. Image signals are then provided through line 42a to controller C'. In some constructions, the power output of each of lasers L-A, L-B and L-C is calibrated using the logic described above in relation to FIGS. 9A and 9B to automatically tune each laser to emit illuminating excitation radiation at substantially the same power level, such as at 200 mw plus or minus 10 mw.

Although specific features of the present invention are shown in some drawings and not in others, this is for convenience only as each feature may be combined with any or all of the other features in accordance with the invention. While there have been shown, described, and pointed out fundamental novel features of the invention as applied to one or more preferred embodiments thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature.

It is the intention, therefore, to be limited only as indicated by the scope of the claims appended hereto. Other embodiments will occur to those skilled in the art and are within the following claims.

What is claimed is:

1. A spectrometer operable to perform an internal calibration check, the spectrometer comprising:
    at least one source of optical radiation operable to generate at least one of:
    (1) an excitation light beam, wherein the excitation light beam comprises an illumination path and at least one of a first collection path and a second collection path, and
    (2) a spectral calibration light beam, wherein the spectral calibration light beam comprises a desired spectral feature and a third collection path;
    a receiving optics unit operable to receive a spectrum of wavelengths derived from at least one of the first collection path and the second collection path, and operable to receive the desired spectral feature derived from the third collection path;
    an imaging device operable to produce image signals from the received spectrum of wavelengths and from the received desired spectral feature;
    a shutter comprising at least one of:
    (1) a first spectral calibration material, the first spectral calibration material operable to alter the excitation light beam in order to generate a first consistent spectrum within wavelengths utilizable by the receiving optics unit and the imaging device in the spectrometer, and
    (2) a mirror, the mirror operable to direct at least two of:
        (a) the illumination path to a second spectral calibration material at a location distinct from the shutter, the second spectral calibration material operable to alter the excitation light beam in order to generate a second consistent spectrum within wavelengths utilizable by the receiving optics unit and the imaging device in the spectrometer, (b) the second collection path extending from the second spectral calibration material toward the receiving optics unit, and
(c) the third collection path toward the receiving optics unit; and a mechanism operatively connected to the shutter and operable to move the shutter into:
(1) at least a first, closed position in the illumination path of the excitation light beam such that a measurement window is blocked and at least one of:
  (a) the excitation light beam strikes the first spectral calibration material wherein the first collection path, comprising the first consistent spectrum, is directed toward the receiving optics unit,
  (b) the excitation light beam is directed by the mirror to the second spectral calibration material,
  (c) the second collection path, comprising the second consistent spectrum, is directed by the mirror toward the receiving optics unit, and
  (d) the third collection path, comprising the desired spectral feature, is directed by the mirror toward the receiving optics unit; and
(2) a second, open position out of the illumination path of the excitation light beam to allow the excitation light beam to strike a sample through the measurement window;
provided that the spectrometer excludes a beam splitter.

2. The spectrometer of claim 1, wherein the source of optical radiation is capable of generating substantially coherent light.

3. The spectrometer of claim 1, wherein the excitation light beam has one of:
a wavelength in the range of 700 nanometers to 1100 nanometers; and
a focal length set for a measurement site located proximate to the measurement window, and in the first, closed position of the shutter, the excitation light beam strikes the first spectral calibration material at a position that is different than the focal length.

4. The spectrometer of claim 1, wherein the spectrometer is capable of performing Raman spectroscopy.

5. The spectrometer of claim 1, wherein the first and second spectral calibration material comprises a polymer.

6. The spectrometer of claim 1, wherein the first and second spectral calibration material comprises polystyrene.

7. The spectrometer of claim 1, wherein the shutter carries at least two different calibration materials, each at a different locus on the shutter, and the mechanism is capable of successively positioning the shutter in different calibration positions, each calibration position corresponding to one of each different locus.

8. A method for calibrating a spectrometer, the method comprising:
positioning a shutter into a first, closed position in an illumination path of an excitation light beam such that a measurement window is blocked, wherein the shutter comprises a mirror, the mirror operable to direct at least two of:
(1) the illumination path of the excitation light beam to a spectral calibration material at a location distinct from the shutter, the spectral calibration material operable to alter the excitation light beam in order to generate a consistent spectrum within wavelengths utilizable by a receiving optics unit and an imaging device in the spectrometer,
(2) a first collection path of the excitation light beam extending from the spectral calibration material, and
(3) a second collection path of a spectral calibration light beam, the spectral calibration light beam comprising at least one desired spectral feature utilizable by the receiving optics unit and the imaging device in the spectrometer;

generating at least one of the excitation light beam and the calibration light beam from one or more light sources such that at least one of:
(1) the illumination path of the excitation light beam strikes the mirror and is directed to the spectral calibration material,
(2) the first collection path of the excitation light beam is directed by the mirror toward the receiving optics unit as a first returned light comprising the consistent spectrum,
(3) the second collection path of the spectral calibration light beam is directed by the mirror toward the receiving optics unit as a second returned light comprising the desired spectral feature;

directing at least one of the first returned light and the second returned light from the receiving optics unit to the imaging device;
processing at least one of the first returned light and the second returned light at the imaging device into one or more image signals;
analyzing and comparing the one or more image signals with approved image signals;
generating comparative results of the analysis; and
providing an indication of whether the comparative results of the analysis are within acceptable tolerances.

9. The method of claim 8, wherein the excitation light beam has one of:
a wavelength in the range of 700 nanometers to 1100 nanometers; and
a focal length set for a measurement site located proximate to the measurement window.

10. The method of claim 8, wherein the spectrometer is capable of performing Raman spectroscopy.

11. The method of claim 8, wherein the spectral calibration material comprises a polymer.

12. The method of claim 8, wherein the spectral calibration material comprises polystyrene.

13. The method of claim 8, further comprising placing a sample at a measurement site located proximate to the measurement window and moving the shutter into a second, open position out of the illumination path of the excitation light beam to take a measurement of the sample.

* * * * *